(12) United States Patent
Moskowitz et al.

(10) Patent No.: US 6,818,669 B2
(45) Date of Patent: Nov. 16, 2004

(54) INCREASING CEREBRAL BIOAVAILABILITY OF DRUGS

(75) Inventors: Michael A. Moskowitz, Belmont, MA (US); James K. Liao, Weston, MA (US); Eyal S. Ron, Lexington, MA (US); Mary Nallin Omstead, Acton, MA (US)

(73) Assignee: Enos Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/955,485

(22) Filed: Sep. 19, 2001

(65) Prior Publication Data

US 2003/0032616 A1 Feb. 13, 2003

Related U.S. Application Data

(63) Continuation of application No. PCT/US00/07089, filed on Mar. 20, 2000.
(60) Provisional application No. 60/139,484, filed on Mar. 19, 1999, provisional application No. 60/138,578, filed on Jun. 11, 1999, and provisional application No. 60/155,485, filed on Sep. 23, 1999.

(51) Int. Cl.[7] ..................... A61K 31/351; A61K 31/198
(52) U.S. Cl. ........................................ 514/460; 514/565
(58) Field of Search ................................. 514/565, 460

(56) References Cited

U.S. PATENT DOCUMENTS

| 4,590,062 A | 5/1986 | Jang ............................. 424/19 |
| 4,882,167 A | 11/1989 | Jang ............................. 424/468 |
| 5,217,997 A | 6/1993 | Levere et al. ........... 514/56245 |

(List continued on next page.)

FOREIGN PATENT DOCUMENTS

| EP | 217379 B1 | 7/1991 |
| EP | 441119 A2 A3 | 8/1991 |
| WO | WO 95/02408 A1 | 1/1995 |

(List continued on next page.)

OTHER PUBLICATIONS

Werner et al., Proceedings of the Society for Experimental Biology and Medicine, 219(3), pp. 171–182 (Dec., 1998) (abstract).*
Myslivacek et al., Neuroscience, 79(3), pp. 659–669 (1997) (abstract).*
Mayhan, W.G. "Role of nitric oxide in histamine–induced increases in permeability of the blood–brain barrier." *Brain Research* 743:70–76 (1996).
Minami, T. et al. "Roles of nitric oxide and the prostaglandins in the increased permeability of the blood–brain barrier caused by lipopolysaccharide." 5:35–41 (1998).
Morikawa, E. et al. "L–arginine dilates rat pial arterioles by nitric oxide–dependent mechanisms and increases blood flow during focal cerebral ischaemia." *Br. J. Pharmacol.* 107:905–907 (1992).

Primary Examiner—Phyllis Spivack
(74) Attorney, Agent, or Firm—Lahive & Cockfield, LLP; Giulio A. DeConti, Esq.; DeAnn F. Smith, Esq.

(57) ABSTRACT

A method and compositions are provided for increased cerebral bioavailability of blood-born compositions by administering the composition of interest while increasing brain NO levels. This increase in NO levels may be accomplished by stimulating increased production of NO by eNOS, especially by administering L-arginine, by administering agents that increase NO levels independent of ecNOS, or by any combination of these methods. As NO is increased, cerebral blood flow is consequently increased, and drugs in the blood stream are carried along with the increased flow into brain tissue. By increased flow, the site of action will be exposed to more drug molecules. By stimulating increased NO production, administration of drugs that are not easily introduced to the brain may be facilitated and/or the serum concentration necessary to achieve desired physiologic effects may be reduced.

7 Claims, 2 Drawing Sheets

U.S. PATENT DOCUMENTS

| | | | |
|---|---|---|---|
| 5,300,288 A | 4/1994 | Albright | 424/78.08 |
| 5,366,738 A | 11/1994 | Rork et al. | 424/473 |
| 5,374,651 A | 12/1994 | Kilbourn et al. | 514/400 |
| 5,385,940 A | 1/1995 | Moskowitz | 514/565 |
| 5,395,612 A | 3/1995 | Griffith et al. | 424/94.6 |
| 5,428,070 A | 6/1995 | Cooke et al. | 514/557 |
| 5,441,946 A | 8/1995 | Pauls et al. | 514/114 |
| 5,470,845 A | 11/1995 | Magnin et al. | 514/121 |
| 5,543,154 A | 8/1996 | Rork et al. | 424/473 |
| 5,543,430 A | 8/1996 | Kaesemeyer | 514/565 |
| 5,576,351 A | 11/1996 | Yoshimura et al. | 514/565 |
| 5,582,838 A | 12/1996 | Rork et al. | 424/472 |
| 5,595,970 A | 1/1997 | Garfield et al. | 514/12 |
| 5,604,256 A | 2/1997 | Kogen et al. | 514/452 |
| 5,643,944 A | 7/1997 | Garfield et al. | 514/470 |
| 5,648,101 A | 7/1997 | Tawashi | |
| 5,693,614 A | 12/1997 | Torii et al. | 514/12 |
| 5,712,396 A | 1/1998 | Magnin et al. | 546/22 |
| 5,767,160 A | 6/1998 | Kaesemeyer | 514/565 |
| 5,788,987 A | 8/1998 | Busetti et al. | 424/480 |
| 5,789,422 A | 8/1998 | Reichard et al. | 514/327 |
| 5,811,416 A | 9/1998 | Chwalisz et al. | 514/177 |
| 5,852,058 A | 12/1998 | Cooke et al. | 514/564 |
| 5,861,168 A | 1/1999 | Cooke et al. | 424/424 |
| 5,876,756 A | 3/1999 | Takada et al. | 424/489 |
| 5,882,682 A | 3/1999 | Rork et al. | 424/473 |
| 5,891,459 A | 4/1999 | Cooke et al. | 424/439 |
| 5,895,783 A | 4/1999 | Garfield et al. | 514/12 |
| 5,895,788 A | 4/1999 | Wideman, Jr. et al. | 514/565 |
| 5,898,032 A | 4/1999 | Yallampalli et al. | 514/742 |
| 5,900,433 A | 5/1999 | Igo et al. | 514/530 |
| 5,906,987 A | 5/1999 | Chwalisz et al. | 514/177 |
| 5,910,482 A | 6/1999 | Yallampalli et al. | 514/12 |
| 5,912,019 A | 6/1999 | Singh | 424/608 |
| 5,945,452 A | 8/1999 | Cooke et al. | 514/564 |
| 5,968,983 A | 10/1999 | Kaesemeyer | 514/564 |
| 5,977,107 A | 11/1999 | Cai et al. | 514/249 |
| 6,028,106 A | 2/2000 | Garfield et al. | 514/561 |
| 6,028,107 A | 2/2000 | Waugh | 514/563 |
| 6,040,340 A | 3/2000 | Chwalisz et al. | 514/509 |
| 6,054,453 A | 4/2000 | Lohray et al. | 514/226.2 |
| 6,063,432 A | 5/2000 | Maxwell et al. | 426/656 |
| 6,117,872 A | 9/2000 | Maxwell et al. | 514/249 |
| 6,127,421 A | 10/2000 | Wideman, Jr. et al. | 514/565 |
| 6,133,320 A | 10/2000 | Yallampalli et al. | 514/632 |
| 6,147,109 A | 11/2000 | Liao et al. | 514/460 |
| 6,165,975 A | 12/2000 | Adams et al. | 514/2 |
| 6,180,597 B1 | 1/2001 | Liao | 514/2 |
| 6,187,744 B1 | 2/2001 | Rooney | 514/6 |
| 6,207,713 B1 | 3/2001 | Fossel | 514/565 |
| 6,210,700 B1 | 4/2001 | Valente et al. | 424/439 |
| 6,239,172 B1 | 5/2001 | Kaesemeyer | 514/460 |
| 6,323,211 B1 | 11/2001 | Garvey et al. | 514/280 |
| 6,350,782 B1 | 2/2002 | Moretti | 514/551 |
| 6,358,536 B1 | 3/2002 | Thomas | 424/608 |
| 6,359,007 B1 | 3/2002 | Pearson et al. | 514/565 |
| 6,391,895 B1 | 5/2002 | Towart et al. | 514/335 |
| 6,423,751 B1 | 7/2002 | Liao | 514/640 |
| 6,425,881 B1 | 7/2002 | Kaesemeyer | 604/93 |
| 6,465,516 B1 | 10/2002 | Kaesemeyer | 514/548 |
| 2003/0114515 A1 | 6/2003 | Kaesemeyer | |

FOREIGN PATENT DOCUMENTS

| | | |
|---|---|---|
| WO | WO 96/10910 A1 | 4/1996 |
| WO | WO 98/08500 A1 | 3/1998 |
| WO | WO 98/44893 A2 | 10/1998 |
| WO | WO 99/59433 A1 | 11/1999 |
| WO | WO 00/20382 A1 | 4/2000 |
| WO | WO 00/23102 A1 | 4/2000 |
| WO | WO 00/29033 A2 A3 | 5/2000 |
| WO | WO 00/40086 A1 | 7/2000 |
| WO | WO 00/45809 A1 | 8/2000 |
| WO | WO 00/56403 | 9/2000 |
| WO | WO 00/59304 A1 | 10/2000 |
| WO | WO 00/62614 A1 | 10/2000 |
| WO | WO 00/74742 A1 | 12/2000 |
| WO | WO 00/74701 A2 A3 | 12/2000 |
| WO | WO 01/28499 A2 A3 | 4/2001 |
| WO | WO 02/00212 A1 | 1/2002 |

* cited by examiner

INCREASING CEREBRAL BIOAVAILABILITY OF DRUGS

This application is a continuation of International Application PCT/US00/07089 filed Mar. 20, 2000, the disclosure being incorporated herein by reference in its entirety. This application is based on U.S. Provisional application No. 60/139,484 filed Mar. 19, 1999, No. 60/138,578 filed Jun. 11, 1999 and No. 60/155,485 filed Sep. 23, 1999.

BACKGROUND OF THE INVENTION

Compounds circulating in the bloodstream of vertebrates cannot freely diffuse into brain tissue due to the blood-brain barrier. This barrier is beneficial in protecting the brain from exogenous influences. However, this beneficial role can become detrimental in a situation requiring therapeutic intervention by a drug with a site of action in the brain, if that drug does not readily cross the blood-brain barrier. For instance, it may not be possible to administer a drug in high enough doses to elevate the systemic levels of the drug blood level sufficiently to achieve a brain blood level effective to produce a desired effect. This situation is particularly likely when the drug sought to be administered to the brain has toxic or unpleasant side effects to the remainder of the body. This problem is exacerbated if the condition requiring therapy is associated with a reduction in blood flow through the brain, such as that occurring due to an ischemic stroke or a cardiovascular event resulting in loss of blood pressure or restricted blood flow to the brain.

Stroke, which is often cited as the third most frequent cause of death in the developed countries, has been defined as the abrupt impairment of brain function caused by a variety of pathologic changes involving one or several intracranial or extracranial blood vessels. Approximately 80% of all strokes are ischemic strokes, resulting from restricted blood flow. Thus, patients afflicted with stroke may especially benefit from increased blood flow and enhanced delivery of anti-stroke and/or neuroprotectant drugs.

Excitotoxic and apoptotic mechanisms have been implicated in the pathophysiology of cerebral ischaemia. MK-801, a glutamate antagonist (non-competitive NMDA channel blocker), protects rat brain from ischaemic cell damage and is the prototype of neuroprotective drugs which enhance resistance to ischemic injury. Neuroprotectants have failed in clinical trials, in part because adequate blood (brain) levels could not be achieved or because of toxicity.

Consequently, reductions in the level of cerebral blood flow may be a significant factor in the uptake of drugs particularly lipophilic drugs, such as MK-801, into brain tissue. Under conditions of ischemia and severely reduced blood flow, the uptake of such drugs is found to be severely reduced. In particular, the potential for achieving therapeutically relevant brain levels of neuroprotective drugs is likely to be severely reduced under circumstances of stroke. Therefore the ability to increase cerebral blood flow and enhance drug delivery, especially under stroke conditions, is highly desirable.

SUMMARY OF THE INVENTION

It is an object of this invention to provide a method for increasing cerebral bioavailability of drugs.

It is an object of this invention to provide a method for increasing cerebral bioavailability of drugs in response to increased cerebral blood flow.

Nitric oxide has been shown to be a vasodilator for the peripheral vasculature in normal tissue of the body. Surprisingly, the present inventors have determined that increasing NO levels via generation of nitric oxide by endothelial nitric oxide synthase (eNOS) and/or non-ecNOS dependent mechanisms also affects the vasculature in brain tissue, causing vasodilation without loss of blood pressure. As a result, release of nitric oxide in the brain vessels causes an increase in blood flow through brain tissue which is not dependent on increases in blood pressure. The present invention uses the blood-pressure-independent increase in blood flow through brain tissue to increase cerebral bioavailability of blood-born compositions.

The present invention provides for increased cerebral bioavailability of blood-born compositions by administering the composition of interest while increasing brain NO levels. This increase in NO levels may be accomplished by stimulating increased production of NO by eNOS, especially by administering L-arginine, by administering agents that increase NO levels independent of ecNOS, or by any combination of these methods. As NO is increased, cerebral blood flow is consequently increased, and drugs in the blood stream are carried along with the increased flow into brain tissue. By increased flow, the site of action will be exposed to more drug molecules. By stimulating increased NO production, administration of drugs that are not easily introduced to the brain may be facilitated and/or the serum concentration necessary to achieve desired physiologic effects may be reduced.

In an important embodiment, the present invention provides for enhanced delivery of drugs to brain tissue by administering the drug of interest (also called the "second agent" or "physiologically active composition (or agent)") while increasing brain NO levels. This increase in NO levels may be accomplished by stimulating increased production of NO by eNOS, especially by administering L-arginine, by administering agents that increase NO levels independent of ecNOS, or by administering any combination of these agents. Preferably, these agents are administered in amounts effective to increase NO levels and/or cerebral blood flow. As NO is increased, cerebral blood flow is consequently increased, and drugs in the blood stream are carried along with the increased flow into brain tissue. By increased flow, the site of action will be exposed to more drug molecules. By stimulating increased NO production, administration of drugs that are not easily introduced to the brain may be facilitated and/or the serum concentration necessary to achieve desired physiologic effects may be reduced.

In one preferred embodiment, this invention provides a method to enhance delivery of a desired composition to brain tissue of an individual comprising introducing the composition into the blood stream of the individual substantially contemporaneously with a blood flow enhancing amount of L-arginine.

In another preferred embodiment, this invention provides a method to enhance delivery of a desired composition to brain tissue of an individual comprising introducing the composition into the blood stream of the individual substantially contemporaneously with a blood flow enhancing amount of L-arginine and/or a blood flow-enhancing amount of a non-ecNOS NO-generating system.

Preferably, agents such as HMG-CoA reductase inhibitors, rho-GTPase inhibitors, and inhibitors of actin cytoskeletal organization are not administered in the methods according to the present invention and are not included in the compositions according to the present invention. Also, preferably, protein kinase C inhibitors, and isoquinoline-sulfonyl compounds or their derivatives, including but not limited to H-7 and H-8 are not administered in the methods according to the present invention and are not included in the compositions according to the present invention. In certain embodiments, cyclosporin-A (Cs-A) is not administered in the methods according to the present invention and is not included in the compositions according to the present invention.

DETAILED DESCRIPTION OF THE EMBODIMENTS

Figure 1:
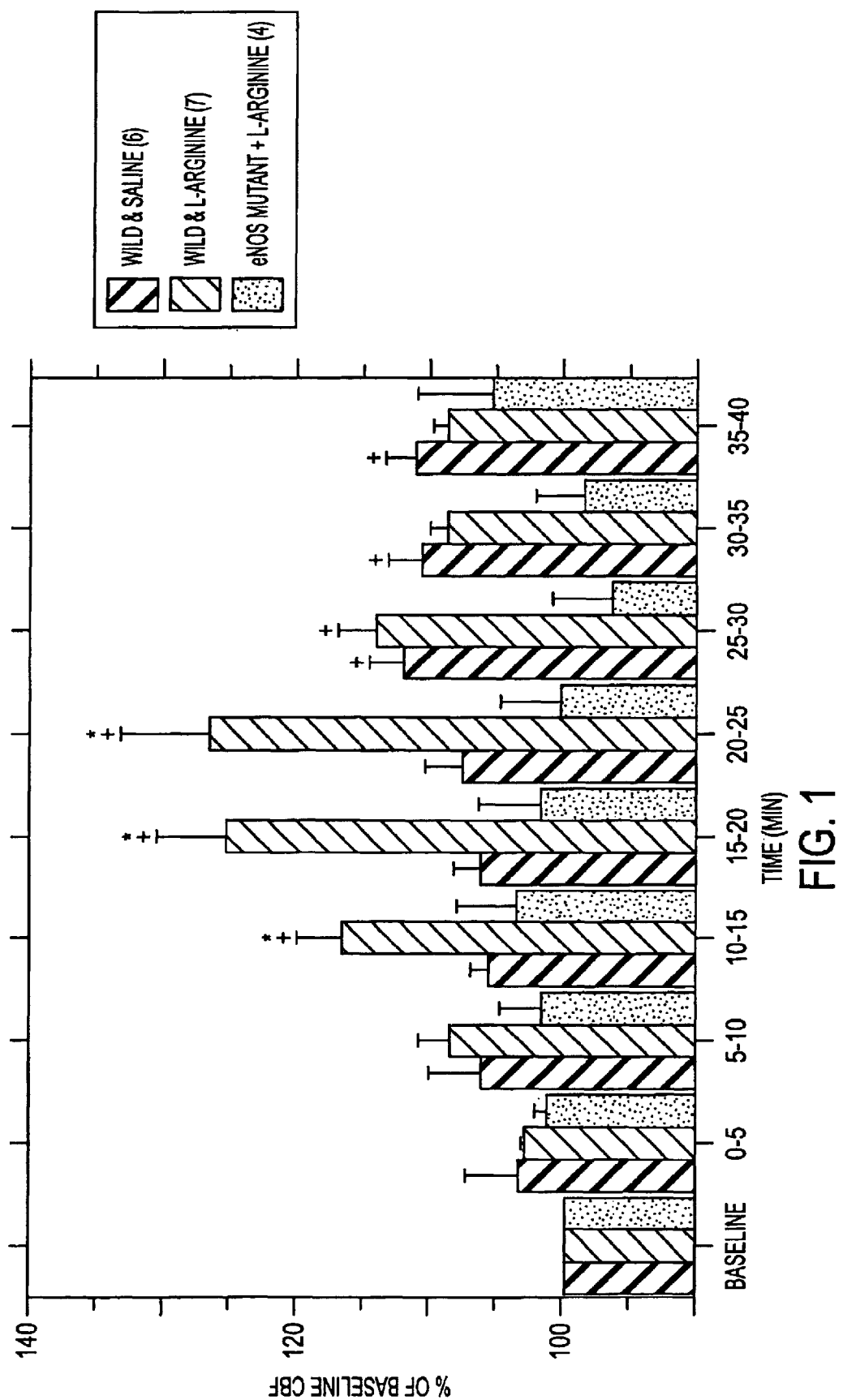
FIG. 1 is a bar graph showing regional cerebral blood flow changes in wild type and mutant mice deficient in endothelial nitric oxide synthase (eNOS null) after L-arginine infusion.

The present invention is useful whenever it is desirable to increase cerebral bioavailability of a drug. A subject as used herein includes humans, non human primates, dogs, cats, sheep, goats, cows, pigs, horses and rodents. The invention thus is useful for therapeutic purposes and also is useful for research purposes such as in testing in animal or in vitro models of medical, physiological or metabolic pathways or conditions.

Nitric oxide (NO) has been recognized as an unusual messenger molecule with many physiologic roles, in the cardiovascular, neurologic and immune systems (Griffith, T M et al., *J Am Coll Cardiol*, 1988, 12:797–806). It mediates blood vessel relaxation, neurotransmission and pathogen suppression. NO is produced from the guanidino nitrogen of L-arginine by NO Synthase (Moncada, S and Higgs, E A, *Eur J Clin Invest*, 1991, 21(4):361–374). In mammals, at least three isoenzymes of NO Synthase have been identified. Two, expressed in neurons (nNOS) and endothelial cells (Type III-ecNOS), are calcium-dependent, whereas the third is calcium-independent and is expressed by macrophages and other cells after induction with cytokines (Type II-iNOS) (Bredt, D S and Snyder, S H, *Proc Natl Acad Sci USA*, 1990, 87:682–685, Janssens, S P et al., *J Biol Chem*, 1992, 267:22964, Lyons, C R et al., *J Biol Chem*, 1992, 267:6370–6374). As the name implies, endothelial cell nitric oxide Synthase refers to the Type III isoform of the enzyme found in the endothelium. The various physiological and pathological effects of NO can be explained by its reactivity and different routes of formation and metabolism.

The present inventors have discovered that the cerebral bioavailability of drugs can be increased by increasing cerebral blood flow. In particular, the present inventors have discovered that the cerebral bioavailability of drugs can be increased by the increased cerebral blood flow brought about by increasing brain NO levels.

Studies by the present inventors support the idea that the cerebral bioavailability of drugs, particularly lipophilic drugs, can be increased by substantially contemporaneous administration of the drug with L-Arginine, other agents which increase NO production by ecNOS, and/or non-ecNOS NO-generating systems. Preferably, these agents are administered in amounts effective to increase NO levels and/or cerebral blood flow. Similarly, for prophylactic use, when the risk of stroke or other brain injury or illness is very high, administration of the compositions according to the present invention will enhance bioavailability of the drug of interest in brain, especially in ischemic brain. Finally, acute, chronic, or prophylactic co-administration of compositions according to the present invention will promote cerebral uptake of drugs for treatment of stroke and other brain disorders or injuries.

L-arginine is a substrate of endothelial nitric oxide synthase (eNOS). Administration of L-arginine will increase the production of nitric oxide (NO) by mass action. Administration of L-arginine results in an increase in cerebral blood flow within minutes. Typically some increase can be observed within ten to fifteen minutes, and a maximum degree of increase may occur within twenty to sixty minutes. The time of maximum effect is a function of both infusion rate and clearance rate. So long as the infusion rate is higher than the clearance rate, maximum L-arginine concentration will be obtained at the end of the infusion.

The present invention provides for increased cerebral bioavailability of drugs by administering the drug of interest while increasing cerebral blood flow by increasing brain NO levels. This increase in NO levels may be accomplished by stimulating increased production of NO by eNOS, especially by administering L-arginine, by administering agents that increase NO levels independent of ecNOS, or by any combination of these agents. Preferably, these agents are administered in amounts effective to increase cerebral NO levels and/or cerebral blood flow. As NO is increased, cerebral blood flow is consequently increased, and drugs in the blood stream are carried along with the increased flow into brain tissue. By increased flow, the site of action will be exposed to more drug molecules. By stimulating increased NO production, administration of drugs to the brain, especially those that that are not easily introduced to the brain, may be facilitated and/or the serum concentration necessary to achieve desired physiologic effects may be reduced.

The level of NO in a cell or in a tissue can be measured in a variety of different ways. One phenotypic measurement employed in the art is detecting endothelial dependent relaxation in response to a acetylcholine, which response is affected by NO level. The level of nitric oxide present in a sample can be measured using a nitric oxide meter. All of the foregoing techniques, as well as additional techniques, are well known to those of ordinary skill in the art.

The present invention, permits not only the re-establishment of normal base-line levels of NO, but also allows increasing NO levels above normal base-line levels. Normal base-line levels are those in a normal control group, controlled for age and having no symptoms which would indicate alteration of nitric oxide levels (such as hypoxic conditions, hyperlipidemia and the like). The actual level then will depend upon the particular age group selected and the particular measure employed to assay activity. In abnormal circumstances, e.g. stroke, nitric oxide levels is depressed below normal levels. Surprisingly, when using the methods and compositions according to the invention, not only can normal base-line levels be restored in such abnormal conditions, but nitric oxide levels can be increased desirably far above normal base-line levels of nitric oxide levels. Thus, in the context of the present invention, "increasing NO levels" encompasses both restoring NO levels to normal baseline levels as well as increasing NO levels above normal baseline levels.

One important embodiment of the invention is treatment of ischemic stroke. Ischemic stroke (ischemic cerebral infarction) is an acute neurologic injury that results from a decrease in the blood flow involving the blood vessels of the brain. Ischemic stroke is divided into two broad categories, thrombotic and embolic.

A surprising finding was made in connection with the treatment of ischemic stroke. In particular, it was discovered that treatment according to the invention can increase blood flow to the brain, even during and after an ischemic stroke. In studies, cerebral blood flow was better in animals treated according to the present invention versus the controls. It is believed that the foregoing positive results are attributable to the increase in nitric oxide levels.

An important embodiment of the invention is treatment of a subject with an abnormally elevated risk of an ischemic stroke. As used herein, subjects having an abnormally elevated risk of an ischemic stroke are a category determined according to conventional medical practice; such subjects may also be identified in conventional medical practice as having known risk factors for stroke or having increased risk of cerebrovascular events. Typically, the risk factors associated with cardiac disease are the same as are associated with stroke. The primary risk factors include hypertension, hypercholesterolemia, and smoking. In addition, atrial fibrillation or recent myocardial infarction are important risk factors As used herein, subjects having an abnormally elevated risk of an ischemic stroke also include individuals undergoing surgical or diagnostic procedures which risk release of emboli, lowering of blood pressure or decrease in blood flow to the brain, such as carotid endarterectomy, brain angiography, neurosurgical procedures in which blood vessels are compressed or occluded, cardiac catheterization, angioplasty, including balloon angioplasty, coronary by-pass surgery, or similar procedures. Subjects having an abnormally elevated risk of an ischemic stroke also include individuals having any cardiac condition that may lead to decreased blood flow to the brain, such as atrial fibrillation, ventrical tachycardia, dilated cardiomyopathy and other cardiac conditions requiring anticoagulation. Subjects having an abnormally elevated risk of an ischemic stroke also include individuals having conditions including arteriopathy or brain vasculitis, such as that caused by lupus, congenital diseases of blood vessels, such as CADASIL syndrome, or migraine, especially prolonged episodes. In certain embodiments, the subject is not hypercholesterolemic or not hypertriglyceridemic or both (i.e., nonhyperlipidemic).

The treatment of stroke according to this invention can be for patients who have experienced a stroke or can be a prophylactic treatment. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects having an abnormally elevated risk of an ischemic stroke, as described above. If the subject has experienced a stroke, then the treatment can include acute treatment. Acute treatment for stroke subjects means preferably administration of a combination according to the invention at the onset of symptoms of the condition or at the onset of a substantial change in the symptoms of an existing condition.

Another important embodiment of the invention, is the treatment of subjects with a neurodegenerative disease. The term "neurodegenerative disease" is meant to include any pathological state involving neuronal degeneration, including Parkinson's Disease, Huntington's Disease, Alzheimer's Disease, and amyotrophic lateral sclerosis (ALS). In preferred embodiments, the neurodegenerative disease is Alzheimer's Disease. Alzheimer's Disease is a progressive, neurodegenerative disease characterized by loss of function and death of nerve cells in several areas of the brain leading to loss of cognitive function such as memory and language. The cause of nerve cell death is unknown but the cells are recognized by the appearance of unusual helical protein filaments in the nerve cells (neurofibrillary tangles) and by degeneration in cortical regions of brain, especially frontal and temporal lobes. Increased cerebral bioavailability of suitable drugs, as provided by the present invention, can be of benefit to subjects suffering from a neurodegenerative disease such as Alzheimer's disease.

Studies by the present inventors support the idea that the cerebral bioavailability of drugs, particularly lipophilic drugs, can be increased by substantially contemporaneous administration of the drug with L-Arginine, other agents which increase NO production by ecNOS, and/or non-ecNOS NO-generating systems. Preferably, these agents are administered in amounts effective to increase brain NO levels and/or cerebral blood flow. Similarly, for prophylactic use, when the risk of stroke or other brain injury or illness is very high, administration of the compositions according to the present invention will enhance bioavailability in brain, especially in ischemic brain. Finally, chronic or prophylactic co-administration of compositions according to the present invention will promote cerebral uptake of drugs for treatment of stroke and other brain disorders or injuries.

The present invention provides for increased cerebral bioavailability of drugs by administering the drug of interest while increasing cerebral blood flow by increasing levels of NO in the brain. This increase in NO levels may be accomplished by stimulating increased production of NO by eNOS, especially by administering L-arginine, by administering agents that increase NO levels independent of ecNOS, or by administration of any combination of these agents. Preferably, these agents are administered in amounts effective to increase NO levels and/or blood flow in or to brain. As NO is increased, cerebral blood flow is consequently increased, and drugs in the blood stream are carried along with the increased flow into brain tissue. By increased flow, the site of action will be exposed to more drug molecules. By stimulating increased NO production, administration of drugs to the brain, especially those that that are not easily introduced to the brain, may be facilitated and/or the serum concentration necessary to achieve desired physiologic effects may be reduced.

In order to increase levels of NO, an agent (preferably L-arginine) which increases ecNOS production by preexisting ecNOS and/or a non-ecNOS NO-generating system is administered to the subject in need of enhanced drug delivery. The combination of an agent which increases ecNOS production by preexisting ecNOS (preferably L-arginine) and/or a non-ecNOS NO-generating system may be referred to herein as an "NO-increasing cocktail." Individually, each of these agents may be referred to as an "NO-increasing agent." Together, these agents may be referred to as "NO-increasing agents."

As used throughout the present application, the terms "NO-increasing cocktail" and "NO-increasing agent(s)" do not include agents such as HMG-CoA reductase inhibitors, rho-GTPase inhibitors, and inhibitors of actin cytoskeletal organization. More detailed definitions of these agents can be found in WO 99/18952, WO 99/47153, and WO 00/03746, which are herein incorporated by reference. Also, as used throughout the present application, the terms "NO-increasing cocktail" and "NO-increasing agent(s)" do not include protein kinase C inhibitors, cyclosporin-A (Cs-A), or isoquinolinesulfonyl compounds or their derivatives, including but not limited to H-7 and H-8.

The NO-increasing agent or cocktail is administered substantially contemporaneously with second agent (the drug whose delivery is sought to be enhanced). In a preferred embodiment, the NO-increasing cocktail comprises L-arginine and at least one non-ecNOS NO-generating system.

The components of the NO-increasing cocktail preferably are administered substantially contemporaneously with one another. As will be noted in more below, "substantially contemporaneous administration" should be interpreted broadly and encompasses many methods of administration. With reference to the components of the NO-increasing cocktail, "substantially contemporaneously" means that the relative timing of administration of the components is coordinated so that a synergistically large increase in NO level is produced in the subject or in a particular tissue of the subject.

Agents used in the present invention need not be administered as one formulation or in one unitary dose or doses in order to be considered to be a "NO-increasing cocktail"; instead, this term includes both combinations of agents which are combined in one unitary dose or formulation and also combinations of agents which are administered in separate doses or formulations, even encompassing agents that are administered via different means (e.g., an NO-increasing cocktail may include an agent which is inhaled or taken orally along with an agent which is administered intravenously).

In order to stimulate increased production of NO by ecNOS, an "ecNOS activating component (or agent)" is administered to the subject in need of enhanced drug delivery. "Agents which increase NO production by ecNOS" and "agents which increase NO production by preexisting ecNOS" are interchangeable terms which also denote ecNOS activating agents. That these agents are referred to as "agents which increase NO production by preexisting ecNOS" does not mean that such agents cannot also increase NO production by ecNOS which is produced during or after administration of these agents; instead the term "preexisting" is meant to indicate that these agents do not themselves increase or upregulate the expression of ecNOS.

The activating component is administered substantially contemporaneously with the drug whose delivery is to be enhanced. A preferred eNOS activating component is an eNOS substrate, such as L-arginine, which drives increased production of NO. Alternative eNOS activating components include cofactors of eNOS, such as NADPH or tetrahydrobiopterin.

Compounds which increase the production of NO by preexisting ecNOS may do so via several different mechanisms. Substrates of ecNOS, such as L-arginine, increase the production of NO by mass action. Cofactors, such as NADPH and tetrahydrobiopterin, increase the production of NO by increasing the ability of ecNOS to catalyze the conversion of substrate to NO. Such ecNOS substrates (e.g. L-arginine) and cofactors (e.g., NADPH, tetrahydrobiopterin, etc.) may be natural or synthetic. Compounds which increase the production of NO by preexisting ecNOS may act cooperatively, additively, or synergistically with agents that increase NO levels via non-ecNOS dependent mechanisms (i.e., non-ecNOS NO-generating systems).

L-arginine is a substrate of endothelial nitric oxide synthase (ecNOS). Administration of L-arginine will increase the production of nitric oxide (NO) by mass action. Administration of L-arginine results in an increase in cerebral blood flow within minutes. Typically some increase can be observed within ten to fifteen minutes, and a maximum degree of increase may occur within twenty to sixty minutes. The time of maximum effect is a function of both infusion rate and clearance rate. So long as the infusion rate is higher than the clearance rate, maximum L-arginine concentration will be obtained at the end of the infusion.

As used throughout the present application, the term "ecNOS activating component" does not include agents such as HMG-CoA reductase inhibitors, rho-GTPase inhibitors, and inhibitors of actin cytoskeletal organization. More detailed definitions of these agents can be found in WO 99/18952, WO 99/47153, and WO 00/03746, which are herein incorporated by reference. Also, as used throughout the present application, the term "ecNOS activating component" does not include protein kinase C inhibitors, cyclosporin-A (Cs-A), or isoquinolinesulfonyl compounds or their derivatives, including but not limited to H-7 and H-8 are not administered in the methods according to the present invention and are not included in the compositions according to the present invention.

NO donors are compounds which release or produce NO or produce NO-related activity, without relying on ecNOS, when administered or applied to biological systems. Feelisch (1998) *Naunyn Schmiedebergs Arch Pharmacol* 358(1): 113–22. Examples of NO donors are well-known in the art and will be described in greater detail below. Inhalation of NO also increases NO levels in a subject.

Non-ecNOS NO generating systems directly increase the levels of NO in a subject, tissue, and/or cell, without relying on ecNOS or other Nitric Oxide Synthases. According to the present invention, "non-ecNOS NO-generating systems" are compounds which, when administered to a subject, increase NO levels in that subject without relying on ecNOS. NO may directly be administered to a subject via inhalation. NO may also be administered to a patient via administration of NO donors. Both NO and NO donors are included in the term "non-ecNOS NO-generating systems."

As used throughout the present application, the term "non-ecNOS NO-generating systems" does not include agents such as HMG-CoA reductase inhibitors, rho-GTPase inhibitors, and inhibitors of actin cytoskeletal organization. More detailed definitions of these agents can be found in WO 99/18952, WO 99/47153, and WO 00/03746, which are herein incorporated by reference. Also, as used throughout the present application, the term "non-ecNOS NO-generating systems" does not include protein kinase C inhibitors, cyclosporin-A (Cs-A), or isoquinolinesulfonyl compounds or their derivatives, including but not limited to H-7 and H-8 are not administered in the methods according to the present invention and are not included in the compositions according to the present invention.

It is a matter of routine optimization for one skilled in the art to select dosages and methods for administration of inhaled NO suitable for use in the methods and compositions according to the present invention. Activities and properties of NO when inhaled are well-known in the art. Administration of inhaled NO to human subjects is described at least in Hoeper, et al., Abman, et al., Carrier, et al., Kinsella, et al., and Kuhlen, et al. See, e.g., Hoeper, et al. (1999) *Respir Med.* 93(1): 62–4; Abman, et al. (1994) *J. Pediatr.* 124(6): 881–8; Carrier, et al. (1999) 18(7): 664–7; Kinsella, et al. (1993) *J. Pediatr.* 122(5 Pt 1): 803–6; and Kuhlen, et al. (1999) *Intensive Care Med.* 25(7): 752–4, the texts of which publications are incorporated herein by reference.

The chemical kinetics of the formation of and methods for reducing the buildup of $NO_2$, a toxic oxidation product of NO, in systems for the delivery of NO by inhalation have been described by several groups. See, e.g., Tsukahara, et al. (1999) *Nitric Oxide* 3(3): 191–8 and Lindberg, et al (1998) *Br. J Anaesth* 80(2): 213–7, the texts of which publications are incorporated herein by reference. Techniques for delivery and monitoring of inhaled NO are also described by several groups. See, e.g., Kirmse, et al. (1998) *Chest* 113(6): 1650–7; Shibata (1996) *Acta Paediatr Jpn* 38(2): 143–6; Young, et al. (1996) *Intensive Care Med.* 22(1): 77–86; and Hess, et al. (1997) *Respir Care Clin N Am* 3(3): 371–410, the texts of which publications are incorporated herein by reference. Technical considerations, including concentrations of the NO gas, are described in the art. See, e.g., Kinsella, et al. (1999) *Curr Opin Pediatr* 11(2): 121–5; Foubert, et al., (1999) *Anaesthesia* 54(3): 220–5; Breuer, et al. (1997) *Eur. J. Pediatr.* 156(6): 460–2; Moon, et al. (1997) *Biomed Instrum Technol* 31(2): 164–8; and Hart (1999) *Chest* 115(5): 1407–17, the texts of which publications are incorporated herein by reference.

As used herein the term "NO donors" refers to a large class of molecules, which have widely varying properties, but which all release or produce NO or produce NO-related activity, without relying on ecNOS, when administered or applied to biological systems. Feelisch (1998) *Naunyn Schmiedebergs Arch Pharnacol* 358(I): 113–22, the text of which publication is incorporated herein by reference. These compounds are well-known in the art. Examples of NO donors include nitroglycerin, nitric oxide/nucleophile adducts (NONOates), including diethylamine/NO complex sodium (Dea/NO) and spermine/NO complex sodium; S-nitrosothiols, also called NO+ equivalents, such as S-nitroso-L-glutathione (GSNO) and S-nitroso-N-acetyl-D, L-penicillamine (SNAP); nitrosylated proteins, such as nitrosylated bovine serum albumin (BSA). See, e.g., Ewing, et al., (1997) *J. Pharmacol. Exp. Ther.* 283(2):947–54; Vidwans, et al. (1999) *J. Neurochem* 72(5): 1843–52, the texts of which publications are incorporated herein by reference. SPM-5185 is an organic cysteine-containing agent which undergoes a biotransformation reaction that releases NO when exposed to physiological conditions. See, e.g., Vinten-Johansen, et al. (1995) *Int. J Cardiol.* 50(3): 273–81, the text of which publication is incorporated herein by reference. Sodium nitrosprusside (SNP) is another NO donor which has been used therapeutically in humans. See, e.g., Thomas, et al. (1999) *Neurosurgery* 44(1):48–57, 57–8; Thomas, et al. (1999) *Stroke* 30(7): 1409–16, the texts of which publications are incorporated herein by reference. Other examples of NO donors include the heterocyclic NO-releasing compounds, which include mesionic heterocycles, such as SIN-1, and heterocyclic N-oxides, such as furoxane carboxamides. See, e.g., Schonafinger (1999) *Farmaco* 54(5): 316–20 and Hou, et al., (1999) *Curr. Pharm. Des.* 5(6): 417–41, the texts of which publications are incorporated herein by reference. Additional NO donors are described in U.S. Pat. No. 5,910,316 to Keefer, et al., U.S. Pat. No. 5,525,357 to Keefer, et al., U.S. Pat. No. 5,356,890 to Loscalzo, et al., and U.S. Pat. No. 5,863,890 to Stamler, et al., the disclosures of which patents are incorporated herein by reference.

It is a matter of routine optimization for one skilled in the art to select NO donors which are suitable for use in the methods and compositions according to the present invention. It is also a matter of routine optimization for a skilled worker in the art to select dosages and modes of administration appropriate to the compositions and methods of the present invention. Activities and properties of NO donors are well-known in the art. For example, Schmidt, et al., have developed a mathematical model for predicting the NO concentrations released from donor compounds over time. Schmidt, et al. (1997) *Naunyn Schmiedebergs Arch Pharmacol* 355(4): 457–62, the text of which publication is incorporated herein by reference. Morley and Keefer provide an in-depth discussion of NONOates, and Kal, et al., describes in detail the administration of nitroglycerin to patients. Morley, et al., (1993) *J. Cardiovasc. Pharmacol.* 22 Suppl. 7: S3-9; Kal, et al. (1999) Anesth. Analg. 88(2): 271–8, the text of which publications are incorporated herein by reference.

Estrogens and ACE inhibitors also increase NO levels. Although estrogens and ACE inhibitors may be used in the methods and compositions according to the present invention, these agents are not included by the terms "agents which increase the production of NO by preexisting ecNOS," "NO-increasing compound," "NO-increasing cocktail," "non-ecNOS NO-generating system," or "ecNOS activating component." Estrogens are a well defined category of molecules known by those of ordinary skill in the art, and will not be elaborated upon further herein. All share a high degree of structural similarity. ACE inhibitors also have been well characterized, although they do not always share structural homology.

Angiotensin converting enzyme, or ACE, is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

In important embodiments, the second agent (i.e., the drug the delivery of which is sought to be enhanced) is co-administered to a subject with a condition treatable by the second agent in an amount effective to treat the condition, whereby the delivery of the second agent to a tissue of the subject is enhanced as a result of the increased blood flow from administering the combination of the invention (at least one non-ecNOS NO-generating system in combination with at least one agent which upregulates ecNOS expression, optionally also combined with other compounds, as described herein, which increase NO levels).

The second agent may be any pharmacological compound or diagnostic agent, as desired. Preferred second agents are agents having a site of action in the brain. Such agents include analeptic, analgesic, anesthetic, adrenergic agent, anti-andrenergic agent, amino acids, antagonists, antidote, anti-anxiety agent, anticholinergic, anticolvunsant, antidepressant, anti-emetic, anti-epileptic, antihypertensive, antifibrinolytic, antihyperlipidemia, antimigraine, antinauseant, antineoplastic (brain cancer), antiobessional agent, antiparkinsonian, antipsychotic, appetite suppressant, blood glucose regulator, cognition adjuvant, cognition enhancer, dopaminenergic agent, emetic, free oxygen radical scavenger, glucocorticoid, hypocholesterolemic, holylipidemic, histamine H2 receptor antagonists, immunosuppressant, inhibitor, memory adjuvant, mental performance enhancer, MAO inhibitor, mood regulator, mydriatic, neuromuscular blocking agent, neuroprotective, neuropsychiatric. NMDA antagonist, post-stroke and post-head trauma treatment, psychotropic, sedative, sedative-hypnotic, selective serotonin uptake inhibitor, serotonin inhibitor, tranquilizer, and treatment of cerebral ischemia, calcium channel blockers, free radical scavengers-antioxidants, GABA agonists, glutamate antagonists, AMPA antagonists, kainate antagonists, competitive and non-competitive NMDA antagonists, growth factors, opioid antagonists, phosphatidylcholine precursors, serotonin agonists, sodium- and calcium-channel blockers, and potassium channel openers.

In addition to the foregoing brain-specific categories of agents, examples of categories of other pharmaceutical agents that can be used as second agents include: adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LNRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine Al antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; treatment of amyotrophic lateral sclerosis; treatment of cerebral ischemia; treatment of Paget's disease; treatment of unstable angina; uricosuric; vasoconstrictor; vasodilator; vulnerary; wound healing agent; xanthine oxidase inhibitor.

Throughout this application, by terms such as "substantially contemporaneous administration," "co-administration," "substantially contemporaneously," and "substantially simultaneously," it is meant that each of the compounds administered are administered to the subject relative in time with one another such that the compounds may exert an additive or even synergistic effect, i.e. on increasing NO levels or on delivering a second agent to a tissue via increased blood flow. These terms may be used interchangeably.

"Substantially contemporaneous administration" as related to enhanced drug delivery refers to administration of a combination for increasing NO levels (as described herein) relative to a second drug, such that the effect of the increased NO levels on cerebral blood flow occurs while the second drug is present in significant serum concentration (i.e., serum concentration adequate for the second drug to have a physiologic effect).

With reference to NO-increasing agents and the components of the NO-increasing cocktail, "substantially contemporaneously" means that the relative timing of administration of the components is coordinated so that a synergistically large increase in NO level is produced in the subject or in a particular tissue of the subject.

"Substantially simultaneous administration" includes the administration of agents (both NO-increasing agents and second agents) as one formulation or unitary dose or doses. "Substantially simultaneous administration" also includes administration of agents in different dosage formats and formulations and at different times, as long as the criteria for substantially simultaneous administration, as noted above, are met.

For example, a combination for increasing NO levels (as described herein) and the second drug may be formulated for i.v. infusion in a single pharmaceutical composition, so that infusion of the pharmaceutical composition puts both a combination for increasing NO levels (as described herein) and the second drug into the bloodstream simultaneously. Preferably, the drug the delivery of which is sought to be increased is in the blood stream while NO levels are increased.

Alternatively, where the second drug is absorbed into the bloodstream upon oral administration at a rate comparable to the absorption of a combination for increasing NO levels (as described herein) orally administered, the two components may be formulated in the same oral composition. If the pharmacokinetics of the second drug are such that significant serum levels are not achieved for several hours, then substantially contemporaneous administration means that a combination for increasing NO levels (as described herein) is administered later, so that the resultant increase in blood flow occurs once significant serum concentration of the second drug has been achieved. Substantially contemporaneous administration of a combination for increasing NO levels (as described herein) and another drug where one or both of the drugs are administered by a nasal, topical, or rectal route, or injected intramuscularly or subcutaneously, or any of the other routes of administration disclosed herein, is a routine matter for one skilled in the art of pharmacology and/or clinical medicine.

The agents (preferably L-arginine) which increase the production of NO by preexisting ecNOS, and/or non-ecNOS NO generating systems are administered in effective amounts. In general, an effective amount is any amount that can cause an increase blood flow in or to the brain, which is typically an amount effective to increase NO levels in the brain.

The second agent or agents are also administered in effective amounts. In general, an effective amount of such an agent is that amount of a pharmaceutical preparation that alone, or together with further doses or co-administration of other agents, produces the desired response. This may involve only slowing the progression of the disease temporarily, although more preferably, it involves halting the progression of the disease permanently or delaying the onset of or preventing the disease or condition from occurring. Such results can be monitored by routine methods.

The effective amount of second agent depends on the particular second agent administered. As a starting point, the effective amounts of second agents are well-known or easily determinable to those of skill in the arts of pharmacology and/or clinical medicine. As it is a goal of the present invention to reduce the amounts of second agents which are needed to accomplish a desired effect, the effective amounts may be modified when the second agent is administered according to the methods of the present invention. In this case, the new effective amounts are determinable with routine experimentation by those skilled in the arts of pharmacology and/or clinical medicine.

The effective amounts of both the NO-increasing agents and the second agents will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

With regard to NO-increasing agents or cocktails, it is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents that increase NO production by preexisting ecNOS, NO, NO donors and other compounds useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include inhalation, oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the active agent(s) into association with a carrier which constitutes one or more accessory ingredients. In general, the compositions are prepared by uniformly and intimately bringing the active compound(s) into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of a NO-increasing agent or cocktail, which is preferably isotonic with the blood of the recipient. The second agent or agents may also be formulated in this composition, or they may be administered in a separate, but substantially simultaneous, manner. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolide), copolyoxalates, polycaprolactones, polyacrylates, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; cellusics; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Particularly preferred embodiments are pre-packaged combinations of NO-increasing increasing agent or agents, NO-increasing cocktails, second agents, and any combination thereof. Even more particularly preferred embodiments are combinations of NO-increasing agent or agents, NO-increasing cocktails, second agents, and any combination thereof which are prepackaged using "Blow/Fill/Seal" technology, as described below.

Blow-Fill-Seal technology, is a manufacturing process that includes the simultaneous filling and closing of the containers by one machine in one operation (some times called also form-fill-seal). This process offers considerable advantages over conventional aseptic filling of preformed (plastic of other) containers by eliminating process steps and performing the whole process in one step in a sterile machine and requires minimal operator intervention. (J. R. Sharp, "Manufacture of Sterile Pharmaceutical Products Using 'Blow-Fill-Seal' Technology", Pharm. J., 239, 106 (1987) F. Leo, "Blow/Fill/Seal Aseptic Packaging Technology in Aseptic Pharmaceutical Technology for the 1990's", Interpharm Press. Prairie View, Ill. 1989, pp. 195–218).

The manufacturing process occurs in a number of stages: In stage 1, polyethelene resin is subjected to high temperature and pressure and is extruded continuously into a tubular shape, which is called a parison. When the tube reaches the proper length, the mold is closed and the parison is cut. The bottom of the parison is pinched closed and the top is held in place. The mold is then conveyed to a position under the blowing and filling nozzle of the sterilized machine. In stage 2, the blow-fill nozzle is then lowered into the parison until it forms a seal with the neck of the mold. The container is formed by blowing filtered compressed air into the parison, expanding it out against the walls of the mold cavity. The compressed air is then vented from the container and a sterile product is metered into the container through the fill nozzle. After the container is filled, the nozzle is retracted to its original position. At this point in the cycle (stage 3), the length of parison at the neck of the hold is semi-molten. Separate sealing molds close to form the top and hermetically seal and form the container. In stage 4, after the container is sealed, the mold is opened. The formed, filled and sealed container is then conveyed out of the machine, and the mold returns to its point of origin to start the next cycle. Additional products may be added to the container at any time prior to or during use via an injection port.

In a preferred embodiment, an NO-increasing agent or cocktail and a second agent is prepackaged in a Blow/Fill/Seal container according to the methods described herein. In another preferred embodiment, an NO-increasing agent or cocktail is prepackaged in a Blow/Fill/Seal container according to the methods described herein. In this embodiment, a second agent or agents may be injected into the container prior to or during administration to a patient. Alternatively, the second agent(s) is administered via another method, such as injection, oral administration, including sublingual administration, inhalation, and the like.

In any of the above embodiments, it is most preferable that the NO-increasing agent is L-arginine or that the NO-increasing cocktail comprises L-arginine.

In such prepackaging embodiments, the amount of NO-increasing agent or cocktail included will preferably be an amount effective to increase NO levels and/or blood flow in the brain of the subject. The amount of second agent included in the prepackaged formulation or administered or added later, will preferably be an amount effective to effect the desired result. It is particularly preferred that the amount of second agent be adjusted to take into account the increased blood flow produced by the NO-increasing agent or cocktail. The effective amount will vary depending on the particular second agent used.

It will, of course, be apparent to the skilled artisan that the considerations involved in formulation pharmaceutical preparations and determining modes of administration of non-ecNOS generating systems are similar to the considerations involved in such formulation and determination for agents which upregulate ecNOS expression and compounds which increase the production of NO by preexisting ecNOS.

More detailed descriptions of endothelial nitric oxide synthase and its regulation, as well as methods of formulating and administering compounds which affect eNOS, such as L-arginine, and the physiologically active compositions of this invention, are provided in publications WO 99/18952, WO 99/47153, WO 00/03746, which are herein incorporated by reference.

EXAMPLES

In order to facilitate a more complete understanding of the invention, a number of Examples are provided below. However, the scope of the invention is not limited to specific embodiments disclosed in these Examples, which are for purposes of illustration only.

Example 1

Effect of L-arginine on Cerebral Blood Flow

L-arginine infusion at 300 mg/kg, i.v., caused modest (10%) and variable elevations in regional cerebral blood flow (RCBF) after infusion in several preliminary experiments (n=4, data not shown). In the present experiments, 450 mg/kg or saline was infused at a constant rate of 100 microliter/kg/min over 15 minutes into wild type mice, mutant mice deficient in endothelial nitric oxide synthase (eNOS null), and mice which had received chronic daily administration of simvastatin (2 mg/kg). Regional cerebral blood flow (rCBF) was monitored by laser-Doppler flowimetry in groups of urethane-anesthetized, ventilated mice. Additional physiological variables were also monitored in the mice, including mean arterial blood pressure (MABP), heart rate, blood pH, PaO2, and PaCO2.

Results

Physiological variables during laser-Doppler flowimetry in urethane-anesthetized ventilated wild type, simvastatin-treated and eNOS null mice infused with L-arginine or saline are shown in Table 1. Number of mice in each group is shown in parenthesis. Values are reported as mean +/− SEM. * denotes statistically significant difference (P<0.05) compared with eNOS null mice; # denotes statistically significant difference (P<0.05) compared with baseline by one-way ANOVA followed by Scheffe test. MABP indicates mean arterial blood pressure; sim indicates mice chronically administered simvastatin.

There were no within-group differences during observation time in mean arterial blood pressure and heart rate, although those values were elevated in eNOS null mice as reported previously. PaCO2 values were not different between two time points in all groups nor between-group, although pH values were lower after infusion of L-arginine.

rCBF Response to L-arginine

FIG. 1 is a bar graph showing regional CBF changes in wild type and eNOS null mice for 40 min after L-arginine (450 mg/kg) or saline infusion at a constant rate of 100 microliter/kg/min over 15 min. The number of mice in each group is indicated in parenthesis. Error bars denote standard error of the mean (SEM), and an asterisk (*) denotes statistically significant difference (P<0.05) compared with baseline control by one-way ANOVA followed by Fisher's protected least-squares difference test.

L-arginine infusion (450 mg/kg, i.v.) increased RCBF in parietal cortex in wild type mice, as shown in FIG. 1 (FIG. 1). The increase in RCBF began at 5–10 minutes and achieved statistical significance at 10–15 minutes after infusion. Maximum values achieved at 20–25 min reached 26% above, after which values decreased to control levels. By contrast, L-arginine did not increase rCBF in eNOS null mice. Values in these mutants ranged from −4 to +5% during the 40 minute recording period. Saline infusion in wild type mice did not increase rCBF significantly.

rCBF Response to L-arginine Plus Simvastatin

Figure 2:
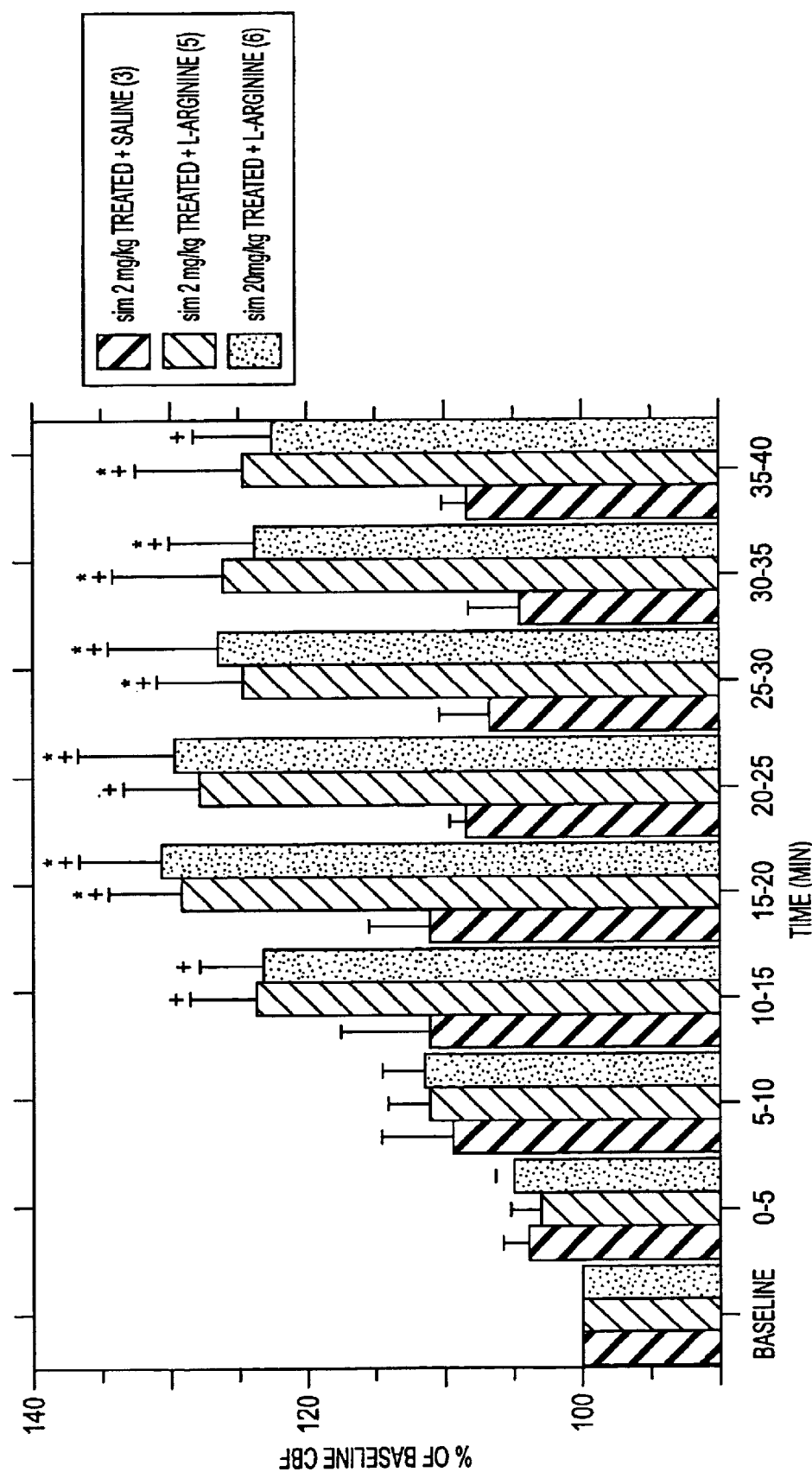
FIG. 2 is a bar graph showing regional cerebral blood flow (rCBF) changes in simvastatin-treated mice after L-arginine infusion.

FIG. 2 is a bar graph showing regional CBF changes in simvastatin-treated mice for 40 min after L-arginine or saline infusion at the same dose. The number of mice in each group is indicated in parenthesis; sim indicates simvastatin. Error bars denote SEM and an asterisk (*) denotes statistically significant difference (P<0.05) compared with baseline control by one-way ANOVA followed by Fisher's protected least-squares difference test.

After chronic daily administration of simvastatin alone, the baseline rCBF was increased by 25%. L-arginine but not saline infusions increased rCBF significantly above the simvastatin baseline. Marked elevation was observed in the 10–15 minute epoch. The maximum increase was observed at 15–20 min and was 29–31% over baseline. These increases sustained for an additional 20 minutes which was considerably longer than after L-arginine treatment alone. The maximum response to L-arginine in the presence of simvastatin was not statistically increased. However, the response to L-arginine was more sustained in the simvastatin-treated mice. In the 30–40 minute epoch, the increase in blood flow was larger in the simvastatin treated compared to non treated control (P<0.05).

TABLE 1

| Group (n) | MABP, mmHg | heart rate, bpm | pH | PaO2, mmHg | PaCO2, mmHg |
| --- | --- | --- | --- | --- | --- |
| wild + saline (6) | | | | | |
| baseline | 94.7 +/− 3.4 | 543 +/− 20 | 7.36 +/− 0.02 | 154 +/− 13 | 35.8 +/− 2.0 |
| 0–5 min | 94.8 +/− 3.3 | 549 +/− 19 | | | |
| 10–15 min | 96.2 +/− 3.2 | 548 +/− 16 | | | |
| 20–25 min | 95.8 +/− 3.1 | 550 +/− 16 | | | |
| 35–40 min | 96.5 +/− 2.9 | 547 +/− 15 | | | |
| after infusion | | | 7.35 +/− 0.02 | 180 +/− 5 | 33.4 +/− 1.8 |
| wild + L-arginine (7) | | | | | |
| baseline | 92.9 +/− 3.5* | 545 +/− 11 | 7.40 +/− 0.02 | 127 +/− 9 | 39.2 +/− 2.0 |
| 0–5 min | 92.7 +/− 3.5 | 548 +/− 11 | | | |
| 10–15 min | 94.6 +/− 3.5 | 561 +/− 9 | | | |
| 20–25 min | 93.3 +/− 3.4 | 554 +/− 10 | | | |
| 35–40 min | 89.9 +/− 3.3 | 533 +/− 9 | | | |
| after infusion | | | 7.32 +/− 0.03 | 169 +/− 5# | 36.4 +/− 1.7 |
| eNOS null + L-arginine (4) | | | | | |
| baseline | 116.3 +/− 9.7 | 618 +/− 9 | 7.40 +/− 0.03 | 15 +/− 4 | 36.4 +/− 1./ |
| 0–5 min | 115.8+/−10.0 | 621 +/− 8 | | | |
| 10–15 min | 113.3 +/− 7.4 | 623 +/− 6 | | | |
| 20–25 min | 113.8 +/− 8.1 | 630 +/− 13 | | | |

TABLE 1-continued

| Group (n) | MABP, mmHg | heart rate, bpm | pH | PaO2, mmHg | PaCO2, mmHg |
|---|---|---|---|---|---|
| 35–40 min after infusion sim (2 mg/kg) + saline (3) | 94.8 +/− 8.1 | 604 +/− 10 | 7.28 +/− 0.04# | 178 +/− 7# | 35.8 +/− 2.4 |
| baseline | 88.0 +/− 3.0* | 541 +/− 1 | 7.46 +/− 0.03 | 159 +/− 19 | 32.7 +/− 2.2 |
| 0–5 min | 90.7 +/− 2.8 | 543 +/− 3 | | | |
| 10–15 min | 93.3 +/− 3.3 | 547 +/− 9 | | | |
| 20–25 min | 95.0 +/− 3.5 | 553 +/− 10 | | | |
| 35–40 min after infusion sim (2 mg/kg) + L-arginine (5) | 94.0 +/− 4.0 | 558 +/− 4 | 7.41 +/− 0.01 | 177 +/− 7 | 32.5 +/− 2.8 |
| baseline | 87.4 +/− 3.1* | 505 +/− 9* | 7.44 +/− 0.03 | 144 +/− 15 | 31.2 +/− 2.8 |
| 0–5 min | 88.4 +/− 3.3* | 503 +/− 7* | | | |
| 10–15 min | 92.2 +/− 3.2 | 507 +/− 6* | | | |
| 20–25 min | 88.4 +/− 3.4* | 502 +/− 5* | | | |
| 35–40 min after infusion sim (20 mg/kg) + L-arginine (6) | 83.8 +/− 4.2 | 490 +/− 4* | 7.30 +/− 0.02# | 163 +/− 13 | 34.2 +/− 2.1 |
| baseline | 91.7 +/− 2.8* | 566 +/− 26 | 7.44 +/− 0.01 | 169 +/− 8 | 32.0 +/− 1.5 |
| 0–5 min | 91.5 +/− 3.7* | 571 +/− 26 | | | |
| 10–15 min | 92.7 +/− 4.9 | 574 +/− 26 | | | |
| 20–25 min | 89.7 +/− 4.9* | 571 +/− 26 | | | |
| 35–40 min after infusion | 84.8 +/− 5.0 | 551 +/− 21 | 7.33 +/− 0.02# | 178 +/− 7 | 32.4 +/− 2.7 |

Example 2

A Composition Containing L-arginine and Simvastatin

L-Arginine (1. g); Simvastatin (0.2 g), sucrose (2. g) and purified water (E-Pure, 1.5 g) are mixed together. The semisolid mixture is stirred until it becomes homogeneous and is dried at 70 C. overnight. The dry mass is ground to particles of roughly 1 mm in dimension. Half of these particles are dipped in 4% solution of ethylcellulose (Benecel) in methyl alcohol and air-dried.

These particles are placed in phosphate buffer saline solution, pH 7.4 at 37 C., and the solution is analyzed at given time points for the presence of L-Arginine.

Example 3

Another Composition Containing L-arginine and Simvastatin

L-Arginine (1 g); Simvastatin (0.2 g), ethylcellulose (Benecel, Hercules, 0.3 g); Avicel (FMC, 0.5 g) and purified water (E-Pure) are mixed together. The semisolid mixture is stirred until it becomes homogeneous and is dried at 70 C. for 4 hours. The dry mass is ground to small particles of roughly 1 mm in dimensions. Half of these particles are tumbled in a granulator and a 4% solution of ethylcellulose (Benecel) in methyl alcohol is gradually added to coat the particles. Then the particles are air dried at 50 C.

The particles are placed in phosphate buffer saline solution pH 7.4 at 37 C. and analyzed at given time points for the release of L-Arginine.

In these two experiments the water insoluble excipient (Benecel and Avicel) will influence the release kinetics of the water-soluble drug and the kinetics are further affected by the coating. Such formulations will allow production of sustained release tablets.

Example 4

A Composition Containing L-arginine and Lotrafiban

Benecel (Hercules, 0.6 g), Avicel (FMC, 0.8 g), magnesium stearate (Mallinckrodt, 0.13 g) are mixed and purified water (E-Pure, 4.9 g) is added to form a dough-like mixture. To this mixture Simvastatin (1 g) and the platelet aggregation inhibitor (blocks glycoprotein IIB/IIIA)—Lotrafiban (SmithKline Beecham, 1 g) are added and mixed in until homogeneous dough is obtained. The resulting semi-solid is granulated to form particles. To these particles Lactose and magnesium stearate are added and compressed into tablets. The tablets are divided into three groups: first group of tablets is left as is; second group is coated with a 50% EudradgitR solution; and the third group is coated with 4% ethylcellulose (Benecel) solution.

In this example Simvastatin provides a chronic delivery platform for Lotrafiban to enhance its therapeutic index.

Example 5

A Composition Containing L-arginine and Clomethiazole

L-Arginine (30 g, 500 mg/kg) and the neuroprotective drug—Clomethiazole (Astra, 4.5 g, 75 mg/kg, GABA agonist) are added to water for injection (300 mL) and the pH is adjusted to 6. The resulting solution is sterile filtered and used as is via intravascular route of administration to treat acute stroke incidence.

In this example L-Arginine provides an acute delivery platform for Clomethiazole to enhance its efficacy and bioavailability.

Example 6

L-Arginine and Simvastatin as Drug Delivery Platforms in vivo 4 groups of mice receive the following treatments by SQ administration for 3 weeks, followed on day 22 by a surgery where an MCA occlusion is induced by an insertion of a modified 8-0 suture. After 15 minutes of occlusion, a tritium labeled Dizocilpine (Glutamate antagonist a non-competitive N-methyl-D-aspartate (NMDA) channel blocker, NeurogardR=AE, MK-801, Merck & Co., Inc.) is injected at a therapeutic concentration (1–3 mg/kg) with or without L-Arginine. Thereafter the mice are sacrificed at 15 and 30 minutes, and the brain tissue is frozen and sectioned and then analyzed by autoradiographic methods to quantitate the amount of radiolabeled compound present within the MCA territory on the side of occlusion.

Treatments
1) 2 groups of saline SC injection over 3 weeks
   a) 1 group after surgery received radio labeled Dizocilpine
   b) 1 group received L-Arginine+radio labeled Dizocilpine
2) 2 groups of Simvastain SC injection over 3 weeks
   a) 1 group after surgery received radio labeled Dizocilpine
   b) 1 group received L-Arginine+radio labeled Dizocilpine L-arginine 400 mg/kg infusion over 10 min.

In this study the group receiving L-Arginine acutely and the group receiving Simvastatin prophylactically have a higher uptake of the neuroprotective drug Dizocilpine within the underperfused brain, where the group receiving Simvastatin prophylactically has the highest uptake of Dizocilpine. This is advantageous, as clinical experience suggests that many of the NMDA antagonists are poorly tolerated at putative neuroprotective doses, and more rapid drug penetration will enhance therapeutic efficacy for NMDA receptor blockers. This is likewise true for all neuroprotective drugs because of the therapeutic window.

Example 7

[3H]MK-801 Uptake into Ischemic Brain 41 male SV-129 mice (20–25 g) were anesthetized with urethane (1 g/kg, i.p.) after induction using halothane. Animals were ventilated to achieve normal arterial blood gases. A femoral artery catheter was inserted to record mean arterial blood pressure, a thermistor was placed to rectally measure core temperature, and arterial blood gases were obtained 5 min prior to middle cerebral artery occlusion (MCAo). The femoral vein was used to bolus inject tritiated MK-801 (New England Nuclear; 22.5 Ci/mmol (100 µL; 1 µCi)) and to infuse L-Arginine (450 mg/kg (100 µL)).

MCA was occluded using the filament technique after introduction of 8-0 monofilament nylon into the external carotid artery, past the orifice of the middle cerebral artery. A laser Doppler flow probe was used to insure that the filament was inserted into the proper place.

Protocol: Four groups were studied: (a) vehicle, (b) simvastatin, (c) L-Arginine, and (d) simvastatin and L-Arginine. Animals in groups (b) and (d) were treated daily with simvastatin (20 mg/kg) for 14 days, not including the day of occlusion. Another group of animals (groups (a) and (c)) received vehicle for the 2-week week duration (subcutaneously). Three minutes following MCAo, animals were infused intravenously with L-arginine or vehicle for a 10-min period. At 15 min after MCAo, the animals were given a bolus injection of tritiated-MK-801 via the femoral vein and sacrificed 10 min later. Total time from MCAo until sacrifice was 25 min (see diagram).

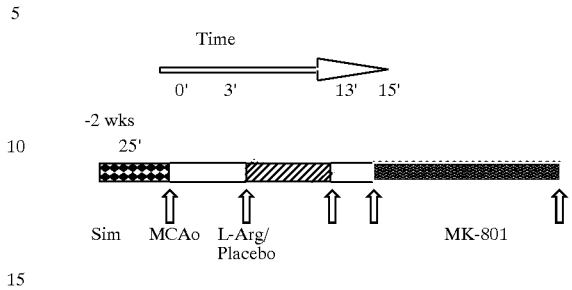

After sacrifice, the brain was quickly removed and immersed into isopentane and cooled on dry ice. The frozen brain was then cut into representative samples (30–40 mg) from the MCA territory on each side. The tissue samples were digested overnight at 50° C. with Scintigest (Fisher Scientific), after which scintillation fluid was added (10 mL) and the sample shaken overnight. Radioactivity was then determined in a liquid scintillation counter (Table 2)

TABLE 2

| Uptake of MK-801 in Mice Brain Tissue after MCA Occlusion | | |
|---|---|---|
|  | Ischemia Side | non-Ischemia Side |
| Vehicle | 600 +/− 240 | 3200 +/− 1500 |
| Simvastatin (20 mg/kg) | 860 +/− 250 | 3250 +/− 700 |
| L-Arginine (450 mg/kg) | 1430 +/− 360 | 3800 +/− 530 |
| Sim + Arg | 1580 +/− 540 | 4600 +/− 1200 |

Data are expressed as cpm/mg tissue.

In more than half of the animals, whole blood samples were obtained to determine blood levels of [3H]MK-801 in each group. Whole blood samples were collected on filter paper every 5 sec for a total of 1 min and then again at 5 and 10 min after isotope injection.

In this study, the uptake of MK-801 into the territory of the occluded middle cerebral artery was increased in mice, under stroke conditions, by 3 fold when the drug was co-administered with L-Arginine. A slightly more pronounced effect was achieved with the combination of Simvastatinl/L-Arginine. Such an increase in bioavailability would promote the success of neuroprotectant drugs that previously failed clinical trials due to low bioavailability in brain, especially if drugs have a low toxic/therapeutic ratio.

The blood samples that were analyzed throughout the study did not reveal any differences between the treated groups. This indicates that the treatment (Simvastatin; L-Arginine and the combination) did not effect the pharmacokinetics (the whole blood distribution) of MK-801.

Example 8

Examples of Specific Formulations

Example 8a. A solution of 30% (w/v) of L-Arginine is sterile-filtered by a 0.22 µm filter. The sterile-filtered solution is metered into a just formed 350-cc polyethylene container through the fill nozzle (300 mL total volume). After that the container is sealed. The solution is used as is to enhance cerebral blood flow of a stroke victim.

Example 8b. L-Arginine (30 g) and the neuroprotective drug—Clomethiazole (Astra, 4.5 g, 75 mg/kg, GABA agonist) are added to water for injection (300 mL) and the pH is adjusted to 6. The resulting solution is sterile filtered and introduced into a just formed in-place 350-cc polypropylene container through the fill nozzle (305 mL total volume). After the container is sealed. The resulting sterile preparation is used as is via intravascular route of administration to treat acute stroke incidence. In this example L-Arginine provides a delivery platform for Clomethiazole to enhance its cerebral bioavailability)

Example 8c. L-Arginine (30 g) and the thrombolytic drug—tissue plasminogen activator (t-PA, GENENTECH, 90 mg) are added to water for injection (300 mL) and the pH is adjusted to pH 7.3. The resulting solution is sterile filtered and introduced into a just formed in-place 350-cc polypropylene container through the fill nozzle (301 mL total volume). After the container is sealed. The resulting sterile preparation is used as is via intravascular route of administration to treat acute stroke incidence. The solution is infused over 60 minutes with 10% of the total dose administered as an initial intravenous bolus over 1 minute. (In this example L-Arginine provides a delivery platform for t-PA to enhance its cerebral bioavailability).

For purposes of clarity of understanding, the foregoing invention has been described in some detail by way of illustrations and examples in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in food science, agricultural engineering, edible oil processing, and/or related fields are intended to be within the scope of the invention, which is limited only by the appended claims. All publications and patent applications mentioned in this specification are indicative of the level of skill of those skilled in the art to which this invention pertains.

What is claimed is:

1. A method of increasing cerebral bioavailability of a simvastatin composition in an individual comprising introducing the composition into the blood stream of the individual substantially contemporaneously with a blood flow enhancing amount of L-arginine.

2. A method of increasing cerebral bioavailability of a simvastatin composition in an individual comprising introducing the composition into the blood stream of the individual substantially contemporaneously with a blood flow enhancing amount of an agent which increases the production of NO by preexisting ecNOS and at least one other NO-increasing agent, wherein the agent which increases the production of NO by preexisting ecNOS is selected from the group consisting of L-arginine, NADPH, and tetrahydrobiopterin.

3. The method according to claim 2, further wherein the agent which increases the production of NO by preexisting ecNOS is L-arginine.

4. The method according to claim 2, wherein the agent which increases the production of NO by preexisting ecNOS is L-arginine and the at least one other NO-increasing agent is a different an agent which increases the production of NO by preexisting ecNOS.

5. The method according to claim 2, wherein the agent which increases the production of NO by preexisting ecNOS is L-arginine and the at least one other NO-increasing agent is a non-ecNOS NO-generating system.

6. The method according to any one of claims 1, 2 and 3–5 wherein the individual has experienced, is experiencing, or has an abnormally elevated risk of experiencing an ischemic stroke.

7. The method according to any one of claims 1, 2 and 3–5 wherein the simvastatin composition has a site of action in the brain.

* * * * *